United States Patent [19]

Koser et al.

[11] 4,348,525
[45] Sep. 7, 1982

[54] COMPOSITION AND A PROCESS FOR THE PREPARATION OF [HYDROXY(ORGANOSULFONYLOXY)I-ODO]ARENES AND THEIR USE IN A REGIOSPECIFIC SYNTHESIS OF DIARYLIODONIUM SALTS

[75] Inventors: Gerald F. Koser, Munroe Falls; Richard H. Wettach, Toledo, both of Ohio

[73] Assignee: The University of Akron, Akron, Ohio

[21] Appl. No.: 252,455

[22] Filed: Apr. 9, 1981

[51] Int. Cl.³ .................. C07D 213/26; C07C 65/01; C07C 139/00
[52] U.S. Cl. .................................... 546/346; 549/29; 549/78; 549/502; 260/545 R; 260/465 G; 562/474
[58] Field of Search ............ 260/545 R, 347.2, 465 G; 546/346; 549/29, 78; 562/474

[56] References Cited

U.S. PATENT DOCUMENTS

| | | | |
|---|---|---|---|
| 3,712,929 | 1/1973 | Jezic | 260/332.5 |
| 3,734,928 | 5/1973 | Jezic | 260/332.5 |
| 3,759,989 | 9/1973 | Jezic | 260/539 |
| 3,801,301 | 4/1974 | Bidlack et al. | 71/76 |
| 3,808,006 | 4/1974 | Smith | 96/88 |
| 3,862,333 | 1/1975 | Chalupa et al. | 424/353 |
| 3,896,140 | 7/1975 | Plepys et al. | 260/307 |
| 3,952,028 | 4/1976 | Jezic | 260/350 |
| 4,136,102 | 1/1979 | Crivello | 260/440 |

Primary Examiner—Natalie Trousof
Assistant Examiner—Frederick W. Pepper
Attorney, Agent, or Firm—Oldham, Oldham, Hudak & Weber Co.

[57] ABSTRACT

[Hydroxy(organosulfonyloxy)iodo]arenes are synthesized in neutral organic solvents by the reaction of ring-substituted [hydroxy(organosulfonyloxy)iodo]benzenes with iodoarenes via ligand transfer. The produced compounds are reacted with (triorganosilyl) arenes or (trihalosilyl)arenes in neutral organic solvents to produce diaryliodonium salts. The diaryliodonium salt synthesis proceeds in regiospecific fashion, aryliodination occurring at the point of attachment of the silicon atom in the silylarenes.

38 Claims, No Drawings

COMPOSITION AND A PROCESS FOR THE PREPARATION OF [HYDROXY(ORGANOSULFONYLOXY)IODO]ARENES AND THEIR USE IN A REGIOSPECIFIC SYNTHESIS OF DIARYLIODONIUM SALTS

TECHNICAL FIELD

The present invention relates to the production of [hydroxy(organosulfonyloxy)iodo]arenes, hereinafter "Hosia" by a ligand transfer reaction in neutral organic solvents. The present invention further relates to the production of diaryliodonium salts produced by the reaction of said Hosia compounds with (triorganosilyl)arenes or (trihalosilyl)arenes, hereinafter, respectively, "TOSA" and "THSA", in neutral organic solvents.

BACKGROUND ART

The compound [hydroxy(tosyloxy)iodo]benzene is known but is a relatively new compound, having first been reported in 1970.

U.S. Pat. No. 3,712,920 relates to 2,5-thiophenediyl-bis(iodonium salts) produced by a condensation reaction in a sulfuric acid medium. It is essential to employ at least a 100 percent molar excess of sulfuric acid. The reactants are a phenyl-2-thienyliodonium trifluoroacetate and a (diacetoxyiodo) benzene. This patent is not pertinent in that not only are the reactants clearly different, but also the reaction must be carried out in sulfuric acid which limits the types of acid-sensitive substituted groups which may be utilized in the reaction.

U.S. Pat. No. 3,734,928 relates to difunctional iodonium salts of diphenyl oxide. Generally, these compounds are prepared by the condensation of (diacetoxyiodo)phenyl ether with thiophene or benzene in the presence of trifluoroacetic acid. This patent contains no suggestion of the reactants of the present invention nor the utilization of a hydrocarbon substituted silane compound.

U.S. Pat. No. 3,759,989 relates to a bis(p-phenoxyphenyl)iodonium trifluoroacetate or trichloroacetate salts. U.S. Pat. No. 3,896,140 relates to 3,5-dimethyl-4-isoxazolyliodonium salts of the formula set forth therein. Similarly, U.S. Pat. No. 3,952,028 relates to bis(dichloroacetoxy)iodobenzenes and bis(trichloroacetoxy)iodobenzenes having the formula set forth therein. All three patents lack the reactants of the present invention as well as the formation of Hosia compounds. These patents further fail to suggest any reaction with (triorganosilyl)arenes and the like.

Moreover, none of the above patents relate to ligand transfer of organoiodine compounds.

DISCLOSURE OF INVENTION

It is therfore an object of the present invention to produce Hosia compounds in neutral organic solvents.

It is a further object of the present invention to produce Hosia compounds, as above, by the reaction of iodoarenes with ring-substituted [hydroxy(organosulfonyloxy)iodo]benzenes via ligand transfer.

It is still another object of the present invention to produce Hosia compounds, as above, wherein good yields are obtained.

It is yet another object of the present invention to utilize Hosia compounds in a regiospecific synthesis of diaryliodonium salts.

It is yet another object of the present invention to produce diaryliodonium salts, as above, by the reaction of the Hosia compounds with (triorganosilyl) arenes or (trihalosilyl)arenes.

It is yet another object of the present invention to produce diaryliodonium salts, as above, in neutral organic solvents.

It is yet another object of the present invention to produce diaryliodonium salts, as above, wherein the reactants contain acid sensitive functional groups.

It is yet another object of the present invention to produce diaryliodonium salts, as above, generally under reflux conditions or under regiospecific control.

These and other objects of the present invention will become apparent from the following specification.

In general, a [hydroxy(organosulfonyloxy)iodo]arene compound has the formula

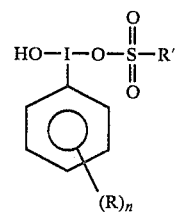

wherein R' is hydrogen, an alkyl having 1 to 20 carbon atoms, an aryl having from 6 to 40 carbon atoms, a halo substituted aryl wherein said aryl has from 6 to 40 carbon atoms; a heterosubstituent substituted aryl wherein said aryl has from 6 to 40 carbon atoms and said heterosubstituent is selected from the group consisting of NO$_2$, CN, COOH, CHO, an alkoxy having from 1 to 6 carbon atoms, an aryloxy having from 6 to 30 carbon atoms, and combinations thereof;

where n of (R)$_n$ is from 0 to 5, wherein said (R)$_n$ groups are the same or different, wherein R is benzo, a halo group, an alkyl group having from 1 to 20 carbon atoms, a cycloalkyl group having from 3 to 20 carbon atoms, an aryl group having from 6 to 40 carbon atoms, a halo aryl group wherein said aryl has from 6 to 40 carbon atoms, an alpha or beta naphthyl, a halo substituted alpha or beta naphthyl, a cycloalkyl substituted alpha or beta naphthyl wherein said cycloalkyl has from 3 to 20 carbon atoms, an alkyl substituted alpha or beta naphthyl wherein said alkyl has from 1 to 20 carbon atoms; a heterosubstituent substituted aryl wherein said aryl has from 6 to 40 carbon atoms, and said heterosubstituent is selected from the group consisting of CN, NO$_2$, COOH, CHO, OH, an alkoxy having from 1 to 5 carbon atoms, an aryloxy having from 6 to 30 carbon atoms, and combinations thereof; a pyridinyl, an alpha or beta furyl or an alpha or beta thienyl.

Generally, a process for preparing an [hydroxy(organosulfonyloxy)iodo]arene comprises the steps of: obtaining a first compound having the formula

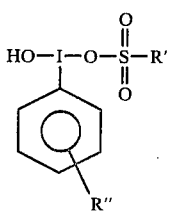

wherein R' is hydrogen, an alkyl having from 1 to 20 carbon atoms, an aryl having from 6 to 40 carbon atoms, a halo substituted aryl wherein said aryl has from 6 to 40 carbon atoms; a heterosubstituent substituted aryl wherein said aryl has from 6 to 40 carbon atoms and said heterosubstituent is selected from the group consisting of $NO_2$, CN, COOH, CHO, an alkoxy having from 1 to 3 carbon atoms, an aryloxy having from 6 to 30 carbon atoms, and combinations thereof;

wherein R" is hydrogen or an ortho, meta, or para alkyl having from 1 to 5 carbon atoms; obtaining a second compound having the formula

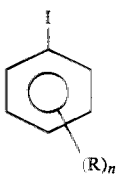

wherein n is from 0 to 5, wherein said $(R)_n$ groups are the same or different, wherein R is benzo, a halo group, an alkyl group having from 1 to 20 carbon atoms, a cycloalkyl group having from 3 to 20 carbon atoms, an aryl group having from 6 to 40 carbon atoms, a halo substituted aryl group wherein said aryl has from 6 to 40 carbon atoms, an alpha or beta naphthyl; a 3 to 20 carbon atom cycloalkyl substituted alpha or beta naphthyl, an alkyl substituted alpha or beta naphthyl wherein said alkyl has from 1 to 20 carbon atoms; a heterosubstituent substituted aryl wherein said aryl has from 6 to 40 carbon atoms, and said heterosubstituent is selected from the group consisting of CN, $NO_2$, COOH, CHO, OH, an alkoxy having from 1 to 5 carbon atoms, an aryloxy having from 6 to 30 carbon atoms, and combinations thereof; a pyridinyl, an alpha or beta furyl or an alpha or beta thienyl; and reacting said first compound and said second compound so that the OH and $SO_3R$ ligands of said first compound are transferred to the iodine atom of said second compound, thereby forming the [hydroxy(organosulfonyloxy)iodo]arene compound.

In general, a diaryliodonium salt comprises a compound having the formula

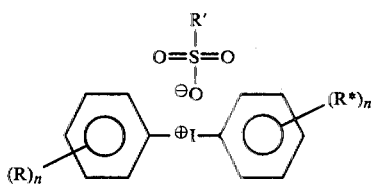

wherein n is from 0 to 5, wherein the $(R)_n$ groups can be the same or different, and wherein R is benzo, H, a halo group, an alkyl group having from 1 to 20 carbon atoms, a cycloalkyl group having from 3 to 20 carbon atoms, an aryl group having from 6 to 40 carbon atoms, a halo substituted aryl group wherein said aryl has from 6 to 40 carbon atoms, an alpha or beta naphthyl, a halo substituted alpha or beta naphthyl, a 3 to 20 carbon atom cycloalkyl substituted naphthyl, an alkyl substituted alpha or beta naphthyl wherein said alkyl has from 1 to 20 carbon atoms; a heterosubstituent substituted aryl wherein said aryl has from 6 to 40 carbon atoms, and said heterosubstituent is selected from the group consisting of CN, $NO_2$, COOH, CHO, OH, an alkoxy having from 1 to 5 carbon atoms, an aryloxy having from 6 to 30 carbon atoms, and combinations thereof; a pyridinyl, an alpha or beta furyl or an alpha or beta thienyl;

wherein R' is hydrogen, an alkyl having from 1 to 20 carbon atoms, an aryl having from 6 to 40 carbon atoms, a halo substituted aryl wherein said aryl has from 6 to 40 carbon atoms; a heterosubstituent substituted aryl wherein said aryl has from 6 to 40 carbon atoms and said heterosubstituent is selected from the group consisting of $NO_2$, CN, COOH, CHO, an alkoxy having from 1 to 6 carbon atoms, an aryloxy having from 6 to 30 carbon atoms, and combinations thereof; and wherein R* is defined by R, and wherein the R* groups are all the same or different.

In general, a process for preparing a diaryliodonium salt comprises the steps of:

obtaining a compound having the formula

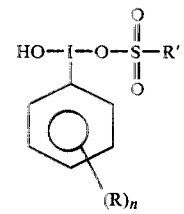

wherein R' is hydrogen, an alkyl having from 1 to 20 carbon atoms, an aryl having from 6 to 40 carbon atoms, a halo substituted aryl wherein said aryl has from 6 to 40 carbon atoms; a heterosubstituent substituted aryl wherein said aryl has from 6 to 40 carbon atoms and said heterosubstituent is selected from the group consisting of $NO_2$, CH, COOH, CHO, an alkoxy having from 1 to 6 carbon atoms, an aryloxy having from 6 to 30 carbon atoms, and combinations thereof;

where n of $(R)_n$ is from 0 to 5, wherein the R groups are the same or different, and wherein R is H, benzo, a halo group, an alkyl group having from 1 to 20 carbon atoms, a cycloalkyl group having from 3 to 20 carbon atoms, an aryl group having from 6 to 40 carbon atoms, a halo substituted aryl group wherein said aryl has from 6 to 40 carbon atoms, an alpha or beta naphthyl; a halo substituted alpha or beta naphthyl, a 3 to 20 carbon atom cycloalkyl substituted alpha or beta naphthyl, an alkyl substituted alpha or beta naphthyl wherein said alkyl has from 1 to 20 carbon atoms; a heterosubstituent substituted aryl wherein said aryl has from 6 to 40 carbon atoms, and said heterosubstituent is selected from the group consisting of CN, $NO_2$, COOH, CHO, OH, an alkoxy having from 1 to 5 carbon atoms, an aryloxy having from 6 to 30 carbon atoms, and combinations thereof, a pyridinyl, an alpha or beta furyl or an alpha or beta thienyl;

obtaining a compound having the formula

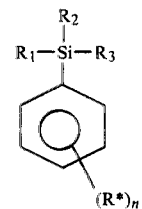

where $R_1$, $R_2$, and $R_3$ are the same or different, where $R_1$, $R_2$, and $R_3$ are a hydrogen, an alkyl having from 1 to 5 carbon atoms, a halo group, an aryl group having from 6 to 24 carbon atoms, or an alkoxy group having from 1 to 5 carbon atoms, or hydrogen;

wherein n of $(R^*)_n$ is from 1 to 5, wherein $R^*$ can be the same or different, and wherein $R^*$ is defined by R; and reacting said compounds and producing a diaryliodonium salt having the formula

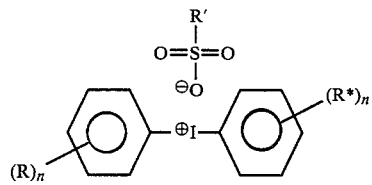

wherein R', $(R)_n$, and $(R^*)_n$ are as set forth herein.

BEST MODE FOR CARRYING OUT THE INVENTION

The starting compounds for the preparation and production of [hydroxy(organosulfonyloxy)iodo]arenes, also referred to as Hosia compounds in this specification, are ring-substituted [hydroxy(organosulfonyloxy)iodo]benzenes having the formula

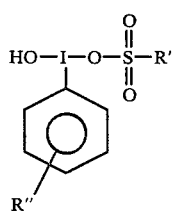

FORMULA 1 wherein R' is a hydrogen or an alkyl having from 1 to 20 carbon atoms, desirably from 1 to 10 carbon atoms. R' may also be an aryl containing from 6 to 40 carbon atoms, preferably from 6 to 20 carbon atoms. R' can also be a haloaryl having from 6 to 40 carbon atoms, etc., wherein the halogen atom is attached either to the benzene ring or to an alkyl substituent of the haloaryl group. R' can further be an aryl (6 to 40 carbon atoms) group substituted with hetero atom substituents (that is other than carbon), for example $NO_2$, CN, COOH, CHO, alkoxy groups having from 1 to 6 carbon atoms, aryloxy groups having from 6 to 30 carbon atoms, and the like. By the term aryl, it is meant an aromatic radical which also can contain, at one or more positions, an alkyl, an aromatic, an alkyl substituted aromatic, an aromatic substituted alkyl, and the like. Examples of specific R' groups include methyl, ethyl, propyl, isopropyl, butyl, phenyl, p-tolyl, p-cumyl, alpha or beta naphthyl, and the like. R'' groups include hydrogen or alkyl having from 1 to 5 carbon atoms and attached ortho, meta, or para to the indicated ring. A highly preferred group is o-methyl since it has been found to increase the solubility of the formula 1 compound. Preferred formula 1 compounds include [hydroxy(tosyloxy)iodo]benzene and [hydroxy(tosyloxy)iodo]o-methylbenzene. It is important that the formula set forth above contains a sulfonyloxy group in order to permit ligand transfer.

The other reactant is an iodoarene generally indicated by the formula

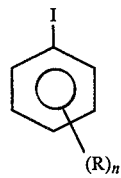

FORMULA 2

Unless otherwise noted, n may be from 0 to 5 groups, preferably 1 or 2 groups, and R is thus attached at any or all of the ring positions, for example, ortho; ortho and para, etc. The R groups can be the same or different. Moreover, R can be a benzo group, for example, 2,3-, 3,4-benzo, or H. The R group can also be halogen, for example, fluoro, chloro, iodo, or bromo. The R group can be an alkyl having from 1 to 20 carbon atoms, desirably 1 to 10 carbon atoms, and preferably from 1 to 5 carbon atoms. Specific examples include ethyl, methyl, propyl, isopropyl, butyl, and the like. Furthermore, cycloalkyl groups may be utilized in the present invention having from about 3 to about 20 carbon atoms, desirably from about 3 to about 10 carbon atoms, and preferably 3 to 5 carbon atoms. Specific examples include cyclopropyl, cyclobutyl, cyclopentyl, cyclohexyl, and the like. Additionally, R can be an aryl group, as defined above, having from 6 to 40 carbon atoms, preferably 6 to 20 carbon atoms, and preferably is attached at the meta or para position. Examples of specific aryl groups include phenyl, tolyl, cumyl, and the like. Similarly, R can be a halogen substituted aryl (6 to 40 carbon atoms, etc.) group having various halogens such as fluoro, chloro, iodo, or bromo, wherein the halogen atom is attached either to the benzene ring or to an alkyl substituent of the aryl group. R also includes alpha or beta naphthyl as well as the alkyl, the halo, and the cycloalkyl substituted naphthyls, with the substituent attached at either the alpha or beta position. The alkyl, halogen, or cycloalkyl substituents thereon are the same as the compounds set forth above, for example, the alkyl can have from 1 to 20 carbon atoms, the cycloalkyl can have from 3 to 20 carbon atoms, and the like. Additionally, R can be aryl groups (6 to 40 carbon atoms, etc.) substituted with hetero atom substituents (that is, other than carbon). For example, nitro $(NO_2)$ groups, nitroso (NO) groups, cyano (CN) groups, carboxyl groups (COOH), aldehydo (CHO), hydroxy (OH) alkoxy groups having from 1 to 5 carbon atoms, aryloxy groups having from 6 to 30 carbon atoms, and the like. Still further examples of compounds which fit the above-noted general description include pyridinyl, alpha or beta furyl, alpha or beta thienyl, and the like.

Of the above numerous R groups, the alkyl, the aryl, and the halo are preferred.

By transfer of the hydroxy and the sulfonyloxy ligand from the iodine (III) atom of the formula number 1 molecule to the iodine (I) atom of the formula number 2 molecule, a product is produced as represented by formula number 3.

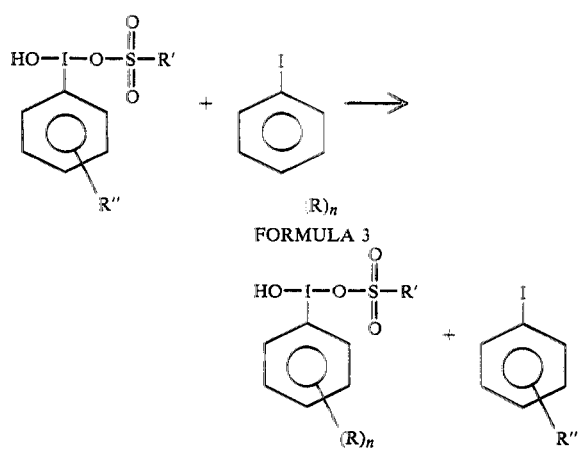

FORMULA 3

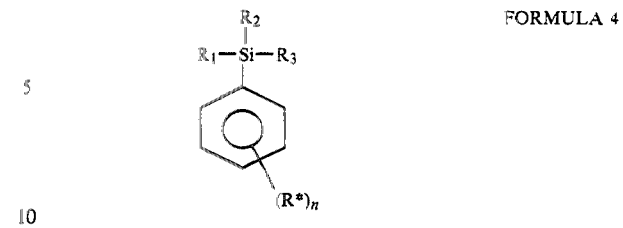

R', R", and (R)$_n$ are as set forth above.

The reaction occurs in relatively neutral organic solvents, for example, solvents having a pH of from about 4 to about 9, and preferably from about 5 to about 8. Thus, (R)$_n$ can be many groups which otherwise the use of acid medium would prohibit. Examples of mild solvents include dichloromethane, acetonitrile, acetic acid, and chloroform, (dichloromethane preferred), and the like, and also dipolar aprotic solvents such as dimethylsulfoxide, dimethylformamide, and the like. Neutral organic solvents are known to those skilled in the art. Reactions can take place at ambient temperature. Generally, the reaction temperature will range from slightly above the freezing point to slightly below the boiling point of the solvent. Generally, the reaction temperature ranges from about 0° C. to about 100° C. with from about 15° C. to about 80° C. being preferred. The pressure is generally atmospheric although it can range from about 0.2 to about 5 atmospheres. Usually, the best yields have been obtained at room temperature. Yield of the desired product is often in excess of 70 or 80 percent. In order to ensure a good yield of the Hosia compound, the mole ratio of the iodoarene to the compound of formula 1 generally ranges from about 0.5 to about 4.0 and preferably is about 1.0.

The Hosia compounds, as represented by formula number 3, generally have antimicrobial properties. Hence, they can be utilized in situations, as set forth hereinbelow.

It is a further aspect of the present invention to react the Hosia compound (#3) with either a (triorganosilyl)arene or a (trihalosilyl)arene, that is respectively "TOSA" or "THSA" in neutral solvents to yield a diaryliodonium salt. The use of neutral organic solvents permits synthesis of iodonium salts bearing acid sensitive groups. This process permits the regiospecific synthesis of diaryliodonium salts with the iodine atom of the Hosia compound being introduced at the point of attachment of the silicon atom in the silane precursor. The silane compound is generally indicated by the formula

FORMULA 4

$R_1$, $R_2$, and $R_3$ can be the same or different groups. $R_1$, $R_2$, and $R_3$ can be hydrogen or an alkyl having from 1 to 5 carbon atoms. Specific examples of alkyl groups include methyl, ethyl, propyl, butyl, and the like. $R_1$, $R_2$, and $R_3$ can also be halo, that is fluoro, chloro, iodo, or bromo. They can also be aryl groups having from 6 to 24 carbon atoms, with 6 to 12 carbon atoms being preferred. Yet another group is alkoxy having from 1 to 5 carbon atoms with specific examples including methoxy, ethoxy, and the like. Preferred $R_1$, $R_2$, and $R_3$ groups include methyl, chloro, phenyl, and the like.

An important aspect of the present invention is that compound 4 requires a silicon substituent so that electrophilic bond cleavage between the arene carbon atom and the silicon atom by Hosia compounds occurs resulting in the production of the diaryliodonium salt.

The (R*)$_n$ substituents of the formula 4 compound can be a wide variety of groups. Generally, the R* groups can be various substituents as set forth above with regard to the R substituents, although R and R* need not be the exact same group, that is, they can be the same or different groups, within the definition. Hence, the entire definition set forth above with respect to R is hereby incorporated. Moreover, R* can be hydrogen. Thus, typical R* groups include an orthomethyl group, a metamethyl group, a paramethyl group, an ethyl group, a propyl group, a phenyl group, and the like. Examples of specific formula 4 compounds include (trimethylsilyl) benzene, o-, m-, or p-(trimethylsilyl)toluene or tetraphenylsilane, and the like. The n of (R*)$_n$ can be from 1 to 5.

The reaction is generally indicated by the following formula

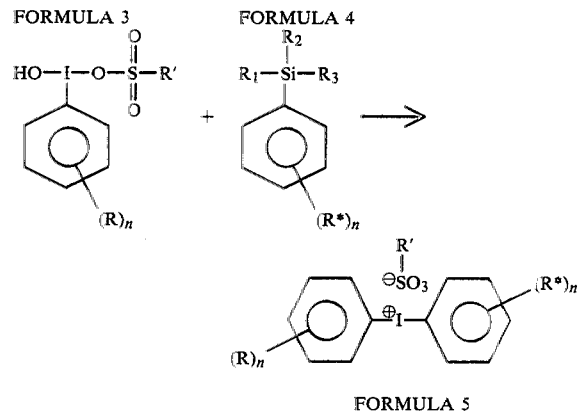

FORMULA 5

Since R', (R), and R* can be a large number of different compounds, plus the fact that R and R* may be located on from 1 to 5 positions of the benzene ring, and may be similar or different, a very large number of diaryliodonium salts can be produced.

The reaction takes place in a neutral organic solvent. The solvents are the same as set forth above with regard to the preparation of the Hosia compounds and thus the same description is applicable. Moreover, the same temperature conditions exist for the reaction with the TOSA or the THSA compounds. That is, the temperature generally ranges from slightly above the freezing point of the solvent to the boiling point of the solvent, and the like. The pressure is generally carried out at atmospheric conditions although vacuum or pressure conditions may exist. Moreover, the atmosphere, in either the preparation of the Hosia compounds or the diaryliodonium compounds can be carried out in an inert gas atmosphere such as nitrogen. It is also desirable to carry out the reaction under reflux as noted above. In other words, the reaction conditions for producing the diaryliodonium salts are the same as set forth above and is thus fully incorporated herein. The amount of the TOSA or the THSA compound, that is compound 4, to the Hosia, formula 3, on a mole ratio is a slight excess, that is from about 0.8 to about 5, desirably from about 0.9 to about 2, and preferably from about 1 to 1, that is a mole ratio of about 1.0. The non-acid route permits a regiospecific synthesis of the diaryliodonium salt (formula 5) to be made by selecting the appropriate TOSA or THSA compound (formula 4) as well as the appropriate Hosia (formula 3). Naturally, the R and the R* groups of formula 5 may be the exact same entities or different.

The various iodonium salts formed according to the present invention have a relatively high toxicity to a broad spectrum of bacteria, fungi, yeast, and small RNA viruses. Moreover, such salts have low toxicity to terrestrial plants and may therefor be applied in bactericidal amounts to obtain excellent control of microbial organisms which attack seeds, roots, or above-ground portions of such plants. Moreover, such compounds in possessing antimicrobial properties can be utilized in adhesives, cooling water, inks, plasticizers, resins, polymer materials, greases, detergents, soap, shampoos, oils, paints (such as latex paints), and the like, to prevent mold and mildew. The compounds of the present invention may further be used in textiles, fabrics, paper, or other cellulosic products and further may be employed in the impregnation of wood, lumber, wallboard, plaster, and the like to prevent attack of bacteria organisms of rot, mold, mildew, and decay.

The invention will be better understood by reference to the following examples.

EXAMPLE 1

Synthesis of 4-[hydroxy(tosyloxy)iodo]chlorobenzene

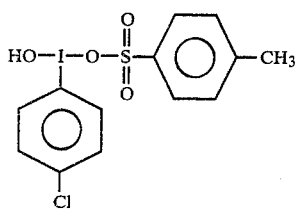

To a solution of p-chloroiodobenzene (0.61 g, 2.5 mmol) in dichloromethane (10 ml) was added [hydroxy(tosyloxy)iodo]benzene (1.00 g, 2.55 mmol). The reaction mixture was allowed to stand for three days at room temperature whereupon the crystals of [hydroxy(toxyloxy)iodo]benzene were replaced by fine needles of [hydroxy(tosyloxy)iodo]p-chlorobenzene. The product was isolated by filtration [yield, 0.98 g (90%)], washed with dichloromethane, acetone and ether, dried in air and recrystallized from acetonitrile; mp 150°-2° (dec).

Analysis: Calculated for $C_{13}H_{12}IClSO_4$: C, 36.59%; H, 2.84%; I, 29.74% Found: C, 36.75%; H, 2.92%; I, 29.69%.

$^1$H NMR (DMSO-$d_6$): δ2.30 (singlet, 3H, tosyloxy methyl); 7.0-8.3 (multiplet, 9H, overlapped AA'BB' patterns with a buried —OH resonance).

EXAMPLE 2

Synthesis of 4-[hydroxy(tosyloxy)iodo]biphenyl

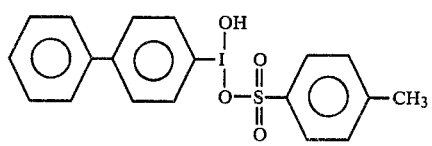

A solution of 4-iodobiphenyl (0.72 g, 2.57 mmol) in dichloromethane (10 ml) was mixed with [hydroxy(tosyloxy)iodo]benzene (1.00 g, 2.55 mmol). After two days standing at room temperature, the crystals of [hydroxy(tosyloxy)iodo]benzene were replaced by fibrous needles of 4-[hydroxy(tosyloxy)iodo]biphenyl suspended in the reaction solvent. The crude product was isolated by filtration and washed with dichloromethane, acetone and ether; yield 0.96 g. Recrystallization from $CH_3CN$ (20 ml)/$CH_3OH$ (2 ml) gave pale brown needles; yield 0.45 g (39%); mp 80°-81° (dec).

Analysis: Calculated for $C_{19}H_{17}ISO_4$: C, 48.73%; H, 3.66%; I, 27.10% Found: C, 48.09%; H, 3.69%; I, 27.09%.

$^1$H NMR (DMSO-$d_6$: δ2.31 (singlet, 3H, tosyloxy methyl); 7.0-8.4 (multiplet, 14H).

Evaporation of the filtrate from the recrystallization and extraction of the residual material with pentane gave 0.34 g (47%) of unreacted 4-iodobiphenyl. Therefore, the yield of product based on unrecovered starting material was 80%.

EXAMPLE 3

Synthesis of [hydroxy(tosyloxy)iodo] β-naphthalene

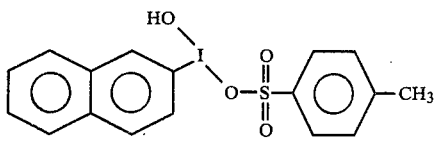

To a solution of β-iodonaphthalene (0.65 g, 2.55 mmol) in dichloromethane (10 ml) was added [hydroxy(tosyloxy)iodo]benzene (1.00 g, 2.55 mmol). After 48 hours at room temperature, the solution was filled with fine crystals of [hydroxy(tosyloxy)iodo] β-naphthalene. The crude product was isolated by filtration and washed with dichloromethane and acetone to give tan crystals; yield 0.84 g (74%), mp 75° (dec). The melting point of the product was unchanged after recrystallization from acetonitrile.

Analysis: Calculated for $C_{17}H_{15}ISO_4$: C, 46.16%; H, 3.42%; I, 28.69% Found: C, 46.00%; H, 3.40%; I, 28.83%.

$^1$HNMR (DMSO-$d_6$): ε2.29 (singlet, 3H, tosyloxy methyl); 7.0-8.4 (multiplet, 12H, aromatic and OH).

EXAMPLE 4

In a similar manner, the following reactants were reacted, usually on a one to one mole basis to yield the indicated product.

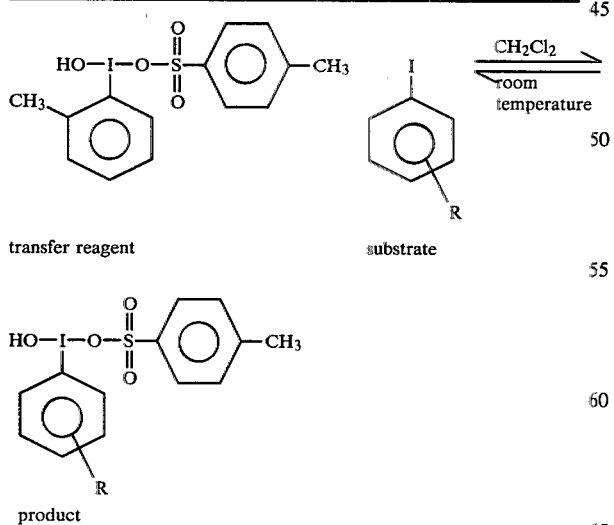

| R | TIME | % YIELD |
| --- | --- | --- |
| 4-Cl | 3 days | 90 |
| 4-Br | 5 days | 85 |
| 4-I | 6 days | 62 |
| 4-Me | | ~85 |
| 4-NO$_2$ | 4 days | 26 (based on unrecovered substrate) |
| 4-Ph | 2 days | 71 (based on unrecovered substrate) |
| 3,4-benzo | 2 days | 74 |
| 2-C(O)—NHMe | 5 days | 91 |
| 2-C(O)—NHCH$_2$Ph | 4 days | 64 |

| R | TIME | % YIELD |
| --- | --- | --- |
| 4-F | ~3 days | 89 |
| 3-NO$_2$ | 24 days | 66 |
| | 2 days | 28 |
| 4-Cl | 3 days | 44 |

EXAMPLE 5

Reaction of o-Trimethylsilyltoluene with [Hydroxy(tosyloxy)iodo]Benzene (HTOB)

(2.00 g, of HTOB, 0.0051 mole) was added to 0.84 g, 0.005 mole o-trimethylsilyltoluene, in CHCl$_3$, 20 ml. The suspension was heated on a steam bath for 20 minutes, and CH$_3$CN (20 ml) was then added down the condenser. The reaction mixture was refluxed for three hours, after which time the condenser water was turned off and the CHCl$_3$ allowed to boil out. The clear yellow solution was then poured into a beaker to evaporate. The residue was dissolved in ca. 5 ml of dry ethanol and ether was added to give a "milky" cloud point. On sitting, the solution deposited 1.00 g of pure white crystals of o-tolylphenyliodonium p-toluenesulfonate; mp 155°–60°; yield 42% PMR(methanol-d$_4$), s, $\delta$2.30(3H); s, 2.55(3H); m, 7.0–8.3(13H). Analysis: Calculated for C$_{20}$H$_{18}$ISO$_3$: %C, 51.62; H, 3.90; I, 27.28. Found: C, 51.22; H, 3.83; I, 26.82.

EXAMPLE 6

Reaction of m-Trimethylsilyltoluene with HTOB (2.00 g of HTOB, 5.1 mmol) was added to 0.86 g, 5.1 mmol, m-trimethylsilyltoluene in ca. 30 ml CH$_3$CN. The mixture was refluxed on a steam bath for eight hours. At that time, the pale yellow solution was poured into a small beaker to evaporate. The solid/liquid residue was redissolved in ca. 20 ml of dry EtOH with warming, and Et$_2$O was then added to just below the cloud point. The clear solution was then set aside for one hour. Fine snow white needles of m-tolylphenyliodonium p-toluenesulfonate; mp 172°–4° C., were isolated; yield, 1.49 g (62%); PMR(methanol-d$_4$), s, $\delta$2.30(6H); m, 7.0–8.2(13H). Analysis: Calculated for C$_{20}$H$_{18}$ISO$_3$: %C, 51.62; H, 3.90; I, 27.28. Found: C, 51.06; H, 3.92; I, 26.99.

EXAMPLE 7

Reaction of p-Trimethylsilyltoluene with HTOB (1.64 g of HTOB, 0.01 mol) p-trimethylsilyltoluene was added to a slurry of 3.92 g, 0.01 mol of HTOB in CH$_3$CN (40 ml) at room temperature. An immediate yellow color formed in the mixture. The slurry was slowly heated with stirring and when a clear solution resulted, it was placed on a steam bath and brought to reflux for four hours. The orange brown solution was then removed from heat and poured into a beaker to evaporate. The residue was washed with ether and finally dissolved in a small volume of EtOH and treated with petroleum ether. On standing, a total of 1.32 g of the p-tolylphenyliodonium p-toluenesulfonate was obtained as tan crystals; mp 153°–5°, yield 35%. PMR(methanol-d$_4$), $\delta$2.30, s(6H, p-tolyl and tosylmethyl); 7.08–8.3 m(13H, aromatic). Analysis: Calculated for C$_{20}$H$_{18}$ISO$_3$: %C, 51.62; H, 3.90; I, 27.28. Found: C, 50.91; H, 4.03, I, 27.03.

EXAMPLE 8

In a similar manner, the following products were made.

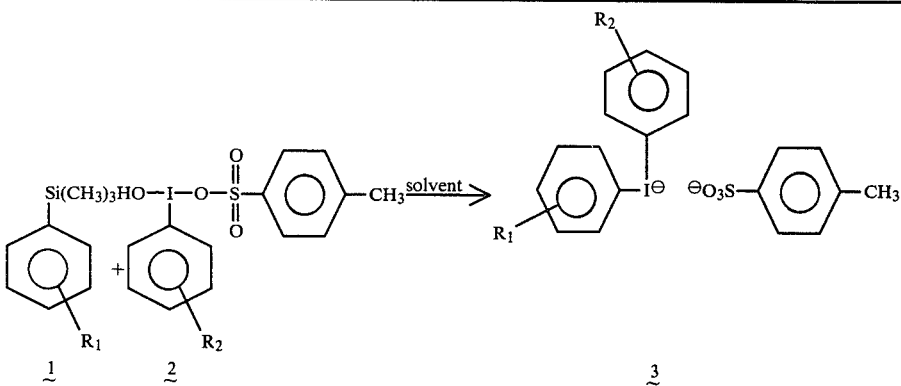

| $R_1$ | $R_2$ | Weight 1(g) | Weight 2(g) | Solvent (vol.ml) | Time | Temp. | Weight 3(g) | % Yield |
|---|---|---|---|---|---|---|---|---|
| H | H | 1.50 | 3.92 | $CH_3CN(25)$ | 6h | reflux | 2.04 | 46 |
| H | H | 0.38 | 1.00 | $CH_2Cl_2$ | several days | room | 0.55 | 48 |
| 2-Me | H | 0.84 | 2.00 | $CH_3CN(20)/CHCl_3(20)$ | 3.33h | reflux | 1.00 | 42 |
| 3-Me | H | 0.86 | 2.00 | $CH_3CN(30)$ | 8h | reflux | 1.49 | 63 |
| 4-Me | H | 1.64 | 3.92 | $CH_3CN(40)$ | 4h | reflux | 1.32 | 29 |
| H | 4-Me | 0.37 | 1.00 | $CH_3CN(25)$ | 5h | reflux | 0.35 | 31 |
| 2-Me | 4-Me | 0.81 | 2.00 | $CH_3CN(25)$ | 6h | reflux | 1.40 | 59 |
| 3-Me | 2-Me | 0.40 | 1.00 | $CH_3CN(25)$ | 9h | reflux | 0.68 | 58 |
| H | 4-Me | 0.37 | 1.00 | $CH_2Cl_2$ | 20h | reflux | 0.20 | 17 |
| 2-Me | 2-Me | 4.00 | 4.02 | $CH_3CN(35)$ | 4h | reflux | 4.00 | 84 (crude) 59 (recryst) |
| 3-Me | 3-Me | 0.80 | 1.98 | $CH_3CN(25)$ | 5h | reflux | 1.81 | 77 (crude) 42 (recryst) |
| 4-Me | 4-Me | 0.80 | 1.99 | $CH_3CN(25)$ | 4h | reflux | 1.85 | 79 (crude) |
| 4-Me | 3-Me | 0.80 | 1.98 | $CH_3CN(25)$ | 3.75h | reflux | 1.92 | 82 (crude) 59 (recryst) |

While having described the best mode and preferred embodiments of the invention, in accordance with the patent statutes, the scope of the invention is not to be limited thereto, the invention being measured by the attached claims.

What is claimed is:

1. A process for preparing a [hydroxy(organosulfonyloxy)iodo]arene compound, comprising the steps of:

obtaining a first compound having the formula

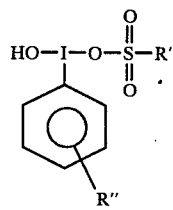

wherein R' is hydrogen, an alkyl having from 1 to 20 carbon atoms, an aryl having from 6 to 40 carbon atoms, a halo substituted aryl wherein said aryl has from 6 to 40 carbon atoms; a heterosubstituent substituted aryl wherein said aryl has from 6 to 40 carbon atoms and said heterosubstituent is selected from the group consisting of $NO_2$, CN, COOH, CHO, an alkoxy having from 1 to 6 carbon atoms, an aryloxy having from 6 to 30 carbon atoms, and combinations thereof;

wherein R" is hydrogen or an ortho, meta, or para alkyl having from 1 to 5 carbon atoms; obtaining a second compound having the formula

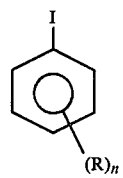

wherein n is from 0 to 5, wherein said $(R)_n$ groups are the same or different, wherein R is benzo, a halo group, an alkyl group having from 1 to 20 carbon atoms, a cycloalkyl group having from 3 to 20 carbon atoms, an aryl group having from 6 to 40 carbon atoms, a halo substituted aryl group wherein said aryl has from 6 to 40 carbon atoms, an alpha or beta naphthyl, a halo substituted alpha or beta naphthyl, a 3 to 20 carbon atom cycle alkyl substituted alpha or beta naphthyl, an alpha or beta alkyl substituted naphthyl wherein said alkyl has from 1 to 20 carbon atoms; a heterosubstituent substituted aryl wherein said aryl has from 6 to 40 carbon atoms, and said heterosubstituent is selected from the group consisting of CN, $NO_2$, COOH, CHO, OH, an alkoxy having from 1 to 5 carbon atoms, an aryloxy having from 6 to 30 carbon atoms, and combinations thereof; a pyridinyl, an alpha or beta furyl or an alpha or beta thienyl; and reacting said first compound and said second compound so that the OH and $SO_3R'$ ligands of said first compound are transferred to the iodine atom of said second compound, thereby forming the [hydroxy(organosulfonyloxy)iodo]arene compound.

2. A process according to claim 1, including carrying out said reaction in a neutral organic solvent.

3. A process according to claim 2, including carrying out said reaction at a temperature of from slightly above the freezing point to the boiling point of said solvent, and wherein the pH of said solvent ranges from about 4 to about 9.

4. A process according to claim 3, wherein the mole ratio of said second compound to said first compound ranges from about 0.8 to about 4.0.

5. A process according to claim 4, wherein said R alkyl contains from 1 to 5 carbon atoms, wherein said R cycloalkyl contains 3 to 5 carbon atoms, and wherein said R aryl contains from 6 to 20 carbon atoms.

6. A process according to claim 4, wherein said R is an alkyl having from 1 to 20 carbon atoms, an aryl having from 6 to 40 carbon atoms, or a halogen selected from the group consisting of fluoro, chloro, iodo, or bromo; and combinations thereof, and wherein n is 1 or 2.

7. A process according to claim 6, wherein said R alkyl has from 1 to 5 carbon atoms, and wherein R aryl has from 6 to 20 carbon atoms.

8. A process according to claim 7, wherein the pH of said solvent ranges from about 5 to about 8, wherein the reaction temperature ranges from about 15° to about 80° C., and wherein the mole ratio of said compound is approximately 1.

9. A process according to claim 3, 4, 6, 7, or 8, wherein said R' is an alkyl having from 1 to 10 carbon atoms, or said R' is an aryl containing from 6 to 20 carbon atoms.

10. A process according to claim 9, wherein said R' is tolyl, and wherein said R" is hydrogen or methyl.

11. A process for preparing a diaryliodonium salt, comprising the steps of:
obtaining a compound having the formula

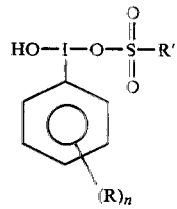

wherein R' is hydrogen, an alkyl having from 1 to 20 carbon atoms, an aryl having from 6 to 40 carbon atoms, a halo substituted aryl wherein said aryl has from 6 to 40 carbon atoms; a heterosubstituent substituted aryl wherein said aryl has from 6 to 40 carbon atoms and said heterosubstituent is selected from the group consisting of $NO_2$, CN, COOH, CHO, an alkoxy having from 1 to 6 carbon atoms, an aryloxy having from 6 to 30 carbon atoms, and combinations thereof;
where n of $R_n$ is from 0 to 5, wherein the R groups are the same or different, and wherein R is benzo, a halo group, an alkyl group having from 1 to 20 carbon atoms, a cycloalkyl group having from 3 to 20 carbon atoms, an aryl group having from 6 to 40 carbon atoms, a halo substituted aryl group wherein said aryl has from 6 to 40 carbon atoms, an alpha or beta naphthyl, a halo substituted alpha or beta naphthyl, a 3 to 20 carbon atom cycloalkyl substituted alpha or beta naphthyl, an alkyl substituted alpha or beta naphthyl wherein said alkyl has from 1 to 20 carbon atoms; a heterosubstituent substituted aryl wherein said aryl has from 6 to 40 carbon atoms, and said heterosubstituent is selected from the group consisting of CN, $NO_2$, COOH, CHO, OH, an alkoxy having from 1 to 5 carbon atoms, an aryloxy having from 6 to 30 carbon atoms, and combinations thereof; a pyridinyl, an alpha or beta furyl or an alpha or beta thienyl;
obtaining a compound having the formula

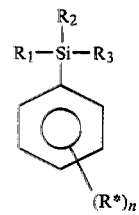

where $R_1$, $R_2$, and $R_3$ are the same or different, wherein $R_1$, $R_2$, and $R_3$ are hydrogen, an alkyl having from 1 to 5 carbon atoms, a halo group, an aryl group having from 6 to 24 atoms, or an alkoxy group having from 1 to 5 carbon atoms;
wherein n of said $(R^*)_n$ is from 1 to 5, wherein $R^*$ can be the same or different, and wherein $R^*$ is defined by R, and
reacting said compounds and producing a diaryliodonium salt having the formula

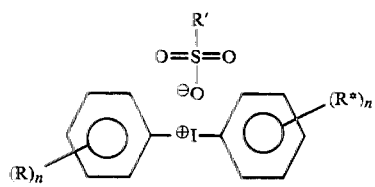

wherein R', $(R)_n$, and $(R^*)_n$ are as set forth herein.

12. A process according to claim 11, including carrying out said reaction in a neutral organic solvent.

13. A process according to claim 12, including carrying out said reaction at a temperature of from slightly above the freezing point to about the boiling point of said neutral solvent, and wherein the pH of said solvent ranges from about 4 to about 9.

14. A process according to claim 13, wherein the mole ratio of said silane containing compound to said iodine containing compound ranges from about 0.8 to about 5.0.

15. A process according to claim 14, wherein R and $R^*$ alkyl group has from 1 to 5 carbon atoms, wherein said R and said $R^*$ aryl group has from 6 to 20 carbon atoms, and wherein said R and said $R^*$ cycloalkyl group has 4 or 5 carbon atoms.

16. A process according to claim 14, wherein R and said $R^*$ is an alkyl having from 1 to 20 carbon atoms, an aryl having from 6 to 40 carbon atoms, or a halogen selected from the group consisting of fluoro, chloro, iodo, or bromo; and combinations thereof, and wherein said $R_1$, $R_2$, and $R_3$ aryl group has from 6 to 12 carbon atoms.

17. A process according to claim 16, wherein said R and said $R^*$ alkyl group has from 1 to 5 carbon atoms, and wherein said R and said $R^*$ aryl group has from 6 to 20 carbon atoms.

18. A process according to claims 12, 14, 16, or 17, wherein the pH of said organic solvent ranges from about 5 to about 8, wherein said reaction temperature ranges from about .15° to about 80° C., and wherein said mole ratio ranges from about 0.9 to about 2.0.

19. A process according to claim 18, wherein R' is an alkyl group having from 1 to 10 carbon atoms, or an aryl group having from 6 to 20 carbon atoms.

20. A process according to claim 19, wherein said R' is tolyl and R" is hydrogen or methyl.

21. A process according to claim 8, wherein said [hydroxy(organosulfonyloxy)iodo]arene is selected from the group consisting of

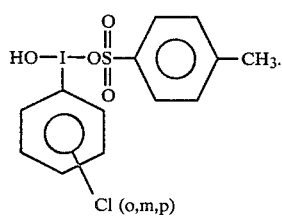

22. A process according to claim 8, wherein said [hydroxy(organosulfonyloxy)iodo]arene is selected from the group consisting of

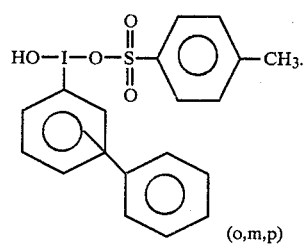

23. A process according to claim 8, wherein said [hydroxy(organosulfonyloxy)iodo]arene is

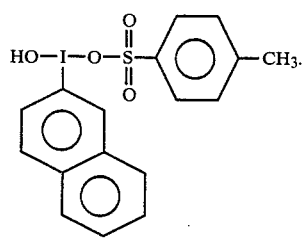

24. A process according to claim 8, wherein said [hydroxy(organosulfonyloxy)iodo]arene is selected from the group consisting of

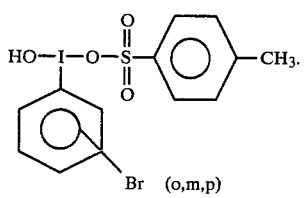

25. A process according to claim 8, wherein said [hydroxy(organosulfonyloxy)iodo]arene is selected from the group consisting of

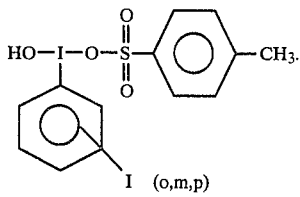

26. A process according to claim 8, wherein said [hydroxy(organosulfonyloxy)iodo]arene is selected from the group consisting of

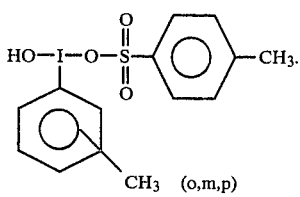

27. A process according to claim 8, wherein said [hydroxy(organosulfonyloxy)iodo]arene is selected from the group consisting of

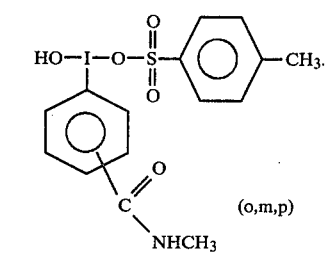

28. A process according to claim 8, wherein said [hydroxy(organosulfonyloxy)iodo]arene is selected from the group consisting of

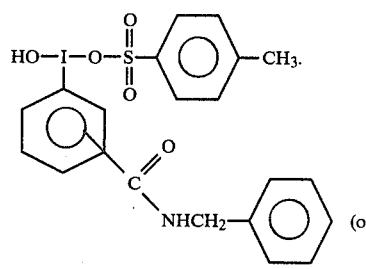

29. A process according to claim 8, wherein said [hydroxy(organosulfonyloxy)iodo]arene is selected from the group consisting of

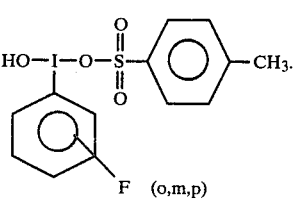

30. A process according to claim 8, wherein said [hydroxy(organosulfonyloxy)iodo]arene is selected from the group consisting of

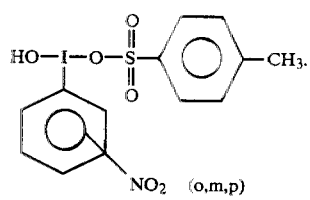

31. A process according to claim 14, wherein said diaryliodonium salt is

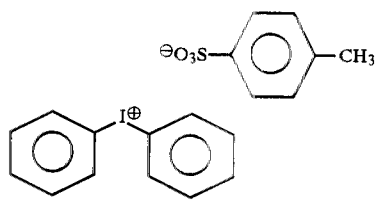

32. A process according to claim 14, wherein said diaryliodonium salt is

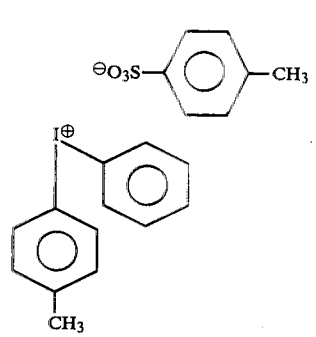

33. A process according to claim 17, wherein said diaryliodonium salt is

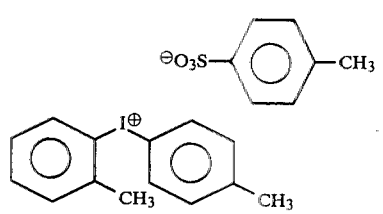

34. A process according to claim 17, wherein said diaryliodonium salt is

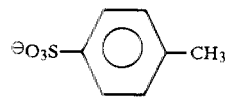
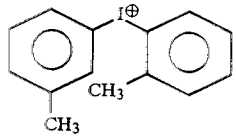

35. A process according to claim 17, wherein said diaryliodonium salt is

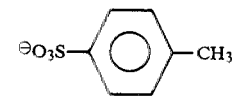
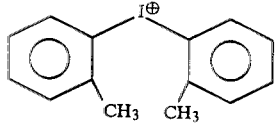

36. A process according to claim 17, wherein said diaryliodonium salt is

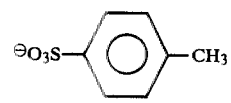
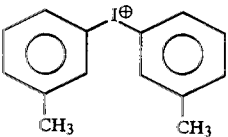

37. A process according to claim 17, wherein said diaryliodonium salt is

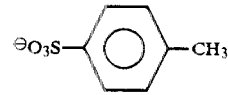
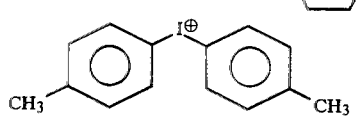

38. A process according to claim 17, wherein said diaryliodonium salt is

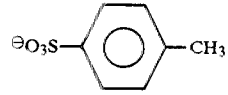
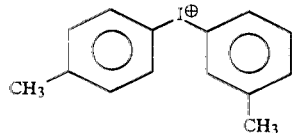

* * * * *

UNITED STATES PATENT OFFICE
CERTIFICATE OF CORRECTION

Patent No. 4,348,525          Dated 9/07/82

Inventor(s) Gerald F. Koser and Richard H. Wettach

It is certified that error appears in the above-identified patent and that said Letters Patent are hereby corrected as shown below:

Claim 1, column 14, line 52, change "cycle alkyl" to --cycloalkyl--.

Signed and Sealed this

Tenth Day of May 1983

[SEAL]

Attest:

GERALD J. MOSSINGHOFF

Attesting Officer          Commissioner of Patents and Trademarks